United States Patent [19]

Ferguson et al.

[11] Patent Number: 4,496,045
[45] Date of Patent: Jan. 29, 1985

[54] MULTI-PANEL FOLDER FOR SURGICAL SUTURES

[75] Inventors: Douglas M. Ferguson; William M. Owens; Michael Lang; Jay P. Lincoln, all of Flagstaff, Ariz.

[73] Assignee: W. L. Gore & Associates, Inc., Newark, Del.

[21] Appl. No.: 620,605

[22] Filed: Jun. 14, 1984

[51] Int. Cl.³ .............................................. A61L 15/00
[52] U.S. Cl. .................................. 206/63.3; 206/476; 206/484; 206/628
[58] Field of Search .................. 206/63.3, 363, 227, 206/628, 476, 484; 128/335.5; 229/88

[56] References Cited

U.S. PATENT DOCUMENTS

| | | | |
|---|---|---|---|
| 3,910,410 | 10/1975 | Shaw | 206/498 |
| 4,014,433 | 3/1977 | Cerwin | 206/63.3 |
| 4,063,638 | 12/1977 | Marwood | 206/63.3 |
| 4,406,363 | 9/1983 | Aday | 206/63.3 |
| 4,413,727 | 11/1983 | Cerwin et al. | 206/63.3 |
| 4,427,109 | 1/1984 | Roshdy | 206/63.3 |

Primary Examiner—Joseph Man-Fu Moy
Attorney, Agent, or Firm—John S. Campbell

[57] ABSTRACT

An improved package for needled sutures comprising a 3-panel folded paper folder for PTFE (and optionally silk, cotton, and other) sutures wherein the suture is arranged in a sinusoidal configuration within the folder and the needle(s) held firmly in place across a U-shaped slot at the top of the folder which allows ready access from either side of the folder when the protective envelopes are opened.

18 Claims, 9 Drawing Figures

MULTI-PANEL FOLDER FOR SURGICAL SUTURES

This application is related to application Ser. No. 620,413, titled Plastic Dispensing Pack For Surgical Sutures, by Jay P. Lincoln, William M. Owens and Douglas M. Ferguson, filed of even date to this application.

BACKGROUND OF THE INVENTION

1. Technical Field

This invention relates to packages for surgical sutures, and more particularly to folded multi-paneled paper board folders and dispensers for certain kinds of sutures having needles attached thereto.

2. Background Art

Packages for surgical sutures having needles attached at one or both ends are constructed according to the nature of the suture material and to how the sutures will be used. Generally, the package holds the suture and attached needles in place, protects them during handling and storage, and allows ready access to the suture for removal with minimum handling at the time the suture is to be used. The suture should also be removable without becoming entangled with itself, kinked or coiled in undesired ways. The nature of the suture material itself may impose limitations on the configuration of the package, how the suture is placed within the package, the placement of the needles, or how the suture is drawn from the package.

A frequently used form of package consists of a folded stiff treated paper suture holder contained in a sterile, hermetically sealed envelope, which envelope is further sealed in a second, usually clear, thermoplastic heat-sealed envelope outer wrap to maintain the suture holder and inner envelope sterile. When the suture is to be used, the outer clear wrap is opened in the operating room and the sealed sterile inner envelope deposited in a sterile area. Sterile personnel then open the inner envelope when access to the suture is needed. A number of these direct dispensing packages represent great advances in the art of surgical suture packaging, but many of them do not address the problems associated with the peculiar properties of sutures manufactured from porous expanded polytetrafluoroethylene (PTFE), which has been prepared in accordance with one or more of U.S. Pat. Nos. 4,187,390; 4,110,392; 4,096,227; 3,962,153 and 3,653,566. Many of the prior packages are not suitable in that crimping, flattening, tangling, or knotting may occur during loading, handling, or removing a PTFE suture from the package. Cuts and slots or other breaks in the surface smoothness in the suture holding area of the paper holder associated with loading or holding a suture tend to damage a PTFE suture drawn across the cut edge. It has been found that mechanically loading a PTFE suture in a package by winding the suture about mandrels or reels in a figure eight or a circular configuration may tend to induce tangling or knotting of the suture upon removing it from the package. Any loading pattern in which the PTFE suture intersects itself can lead to knotting. Friction pads, such as those made from polymer foam and used to hold the sutures in place, also tend to induce tangling and knotting. Cotton and silk sutures have also been found to sometimes tangle or knot under the same circumstances as PTFE sutures and hence the suture folder of this invention can be usefully employed for sutures manufactured from cotton, silk or any pliable suitable material. Additionally, although many suture packages attempt to fix any attached needles in a particular location for easy presentation to the user, it has been found that often the needles become dislodged and are not conveniently presented to the user. If the needles do remain fixed in place, they are often accessible from one direction only. Typical folders and packages for sutures representative of the art are disclosed in U.S. Pat. Nos. 4,253,563; 4,284,194; 4,063,638; 4,089,410; and 4,369,880.

Thus, the suture package of this invention has several advantages over the prior art packages for PTFE sutures. The advantage of non-overlapping of PTFE suture strands is combined with holding of the needles in a fixed position in a unique orientation which presents the needles in such a way that they may be gripped from either side of the package by a needle holder. Right-handed or left-handed removal of the needle and suture is equally facile. The needles are immediately visible in a slot in the top of the suture folder on only partial peeling back of the inner protective envelope and can be immediately gripped in the slot from either side of the folder and the suture easily withdrawn from the folder without further opening of either the protective envelope or the paper folder.

SUMMARY OF THE INVENTION

The present invention is characterized by a 3-part folded paper folder for a suture with one or two attached needles sealed in an inner protective envelope and having an outer clear protective envelope. The paper suture folder has a first panel foldably connected to a second panel along a major edge and a third panel foldably connected along a major edge to the second panel along its major edge opposite the edge connected to the first panel. The first panel has chamfered upper corners, a U-shaped notch in the center of the upper edge, an incised slit in the top portion of the panel near the edge foldably joined to the second panel, a fold line across the panel near the bottom, and a clearance notch in the lower corner at the fold line joining the first and second panels. The second panel has chamfered upper corners, a U-shaped notch in the center of the upper edge which will register with the like notch in the first panel when the folder is folded together, an integral incised tab to the left of the notch, an incised aperture to the right of the U-shaped edge slot, a small punched out circular aperture below and to the left of the incised tab near the fold line of the first and second panels, and an incised interlocking tab in the center of the lower edge of the panel. The third panel has a chamfered upper corner at the fold line with the second panel, is contoured so as to avoid overlapping the U-shaped notches of the first and second panels when the third panel is folded over them, a corner or adjacent panel edge is inserted into the cut incised slit of the first panel to hold the third panel in place when folded over the first panel, and an incised interlocking tab in the center of the lower edge of the panel which is interlocked with a like tab in the lower edge of the second panel when the panels are folded over the second panel. The needle or needles attached to a suture are placed point first in the incised aperture of the second panel, outside to inside, the shank held behind the incised tab on the opposite side of the U-shaped edge slot, and the attached suture disposed in a sinusoidal pattern down the length of the second panel. The bottom of the first panel is folded upwardly along the fold line, the first panel folded over the suture and needles in place on the second panel, the third panel folded over the first panel, the center corner or adjacent panel edge inserted in the incised slit of the first panel, and the interlocking incised tabs of the second and third panels interlocked. The folded-up bottom portion of the first panel is held in place by the interlocking tabs of the second and third panels to provide an effective bottom closure to the folder. The preferred embodiments of the invention have the needles always firmly held in the same position and direction across the U-shaped slot, readily available for use from either side of the folder for right or left-handed removal, and the PTFE or optionally silk, cotton or any pliable suitable suture material for which the folder is intended lying in a sinusoidal configuration to avoid tangling or knotting on removing the suture from the package. The folder of this invention can also be used with sutures other than those for which its design is particularly and specifically intended.

Other and further advantages of this invention will appear to one skilled in the art from the following description and claims together with the drawings.

DESCRIPTION OF THE PREFERRED EMBODIMENTS

Figure 1:
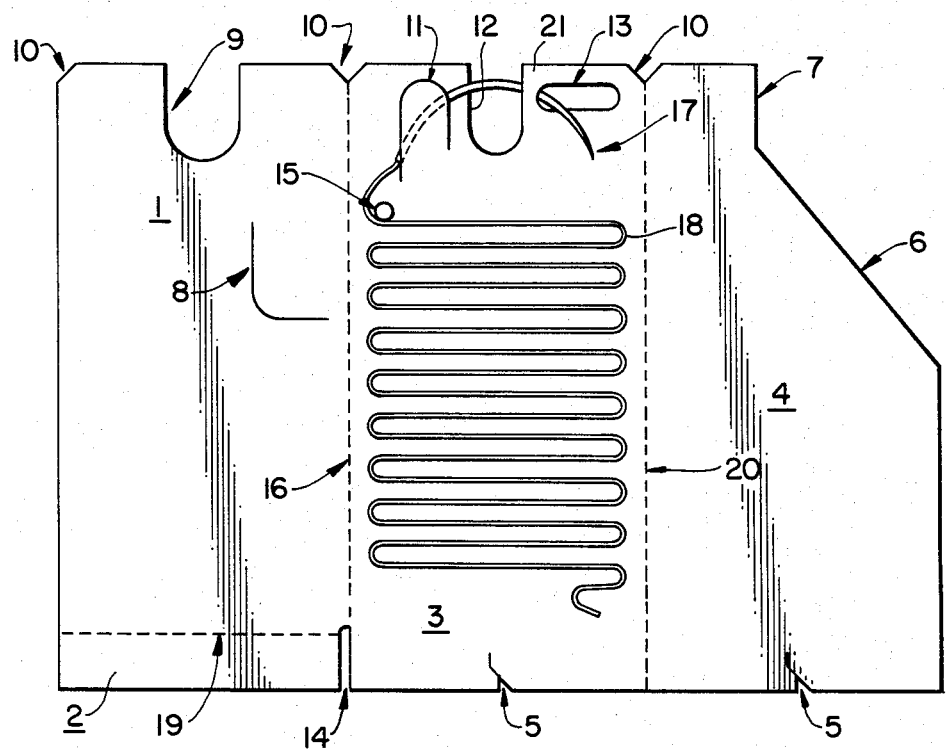
FIG. 1 is a front plan view of the unfolded suture folder of the invention shown containing a suture with one needle attached.

Referring now to the drawings, identical numerals are used for identical parts in each of the figures to aid in the description of the suture folder of the invention. FIG. 1 shows the 3-panel foldable folder of the invention in unfolded position. The first panel 1 is attached along fold line 16 to the second panel 3, has chamfered upper corners 10, a U-shaped slot 9, an incised slit 8, and a cut out corner 14 for clearance with the other panels when the folder is folded together. The lower part 2 of panel 1 has a fold line 19 along which lower part 2 is folded back on the remainder of panel 1 to form a suture-retention bottom to the folded folder. The second panel 3 also has chamfered upper corners 10, a cut tab 11, an incised aperture 13, a U-shaped slot 12 spaced to be in register with slot 9 of panel 1 when the panels are folded together, an incised interlocking tab 5 for interlocking with similar tab 5 on the third panel 4, punched out aperture 15 for registration means for loading of suture in the folder, and fold line 20 where the third panel 4 joins panel 3. The third panel 4 is chamfered at corner 10, is cut away along sides 7 and 6 so as to not cover the needle access slots 9 and 12 when the folder is folded together around a suture and needle and to provide an edge 6 for insertion in incised slit 8 on full closure, and an incised interlocking tab 5 which interlocks with tab 5 on panel 3 at closure. A suture 18 is shown laid out in sinusoidal configuration on panel 3 past register aperture 15 and attached to needle 17, which is held in place behind tab 11 across slot 12 and behind the edge of slot 12 into aperture 13. Tab 11 and the portion 21 of panel 3 which crosses the needle 17 between slot 12 and aperture 13 exert a holding force on the needle 17 when held in panel 3 and when the folder is closed for packaging.

Figure 2:
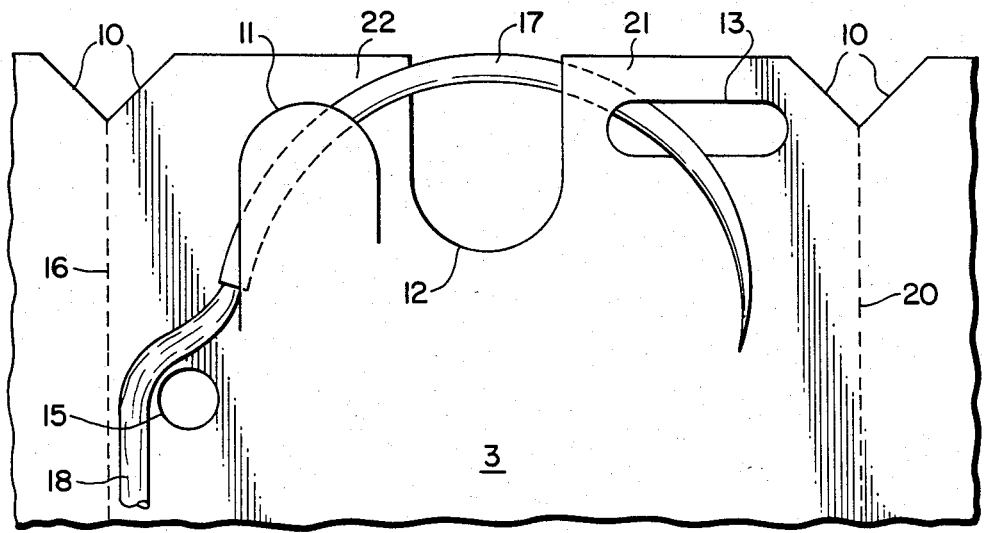
FIG. 2 is a plan view of a needle held in position by the incised tab and incised aperture.

FIG. 2 gives in close detail the relationship between needle 17 and the parts of panel 3 which hold it firmly in place: tab 11, slot 12, aperture 13, and panel portions 21 and 22, all of which together combine to exert the holding force.

Figure 3:
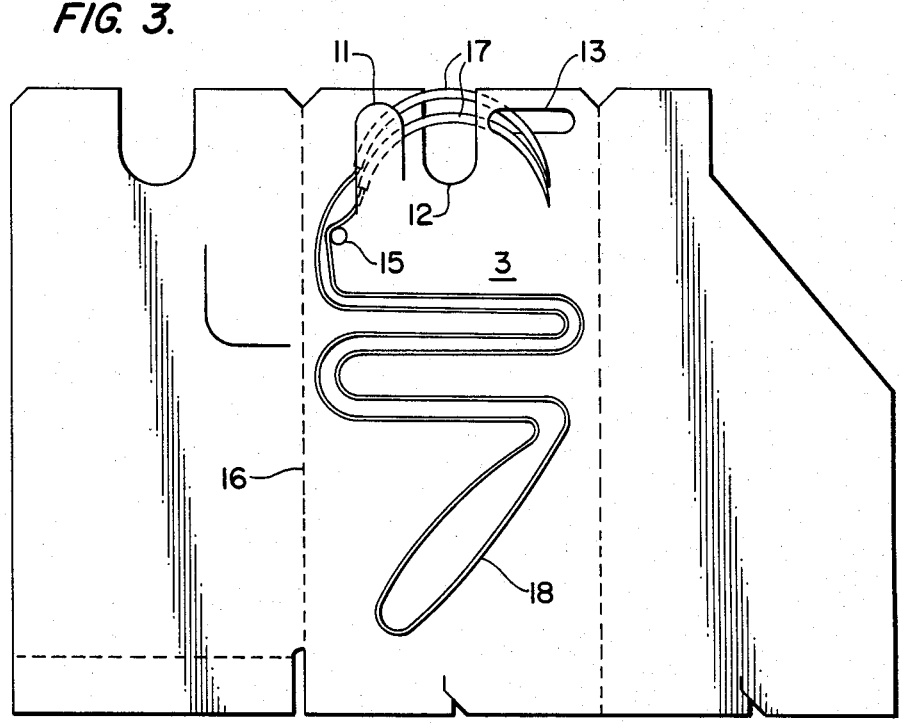
FIG. 3 shows a suture with a needle attached at each end being held in position with both needles held together in the incised tab and incised aperture.

FIG. 3 shows a suture in place on panel 3 with needles 17 affixed at each end and coiled in sinusoidal configuration.

Figure 4:
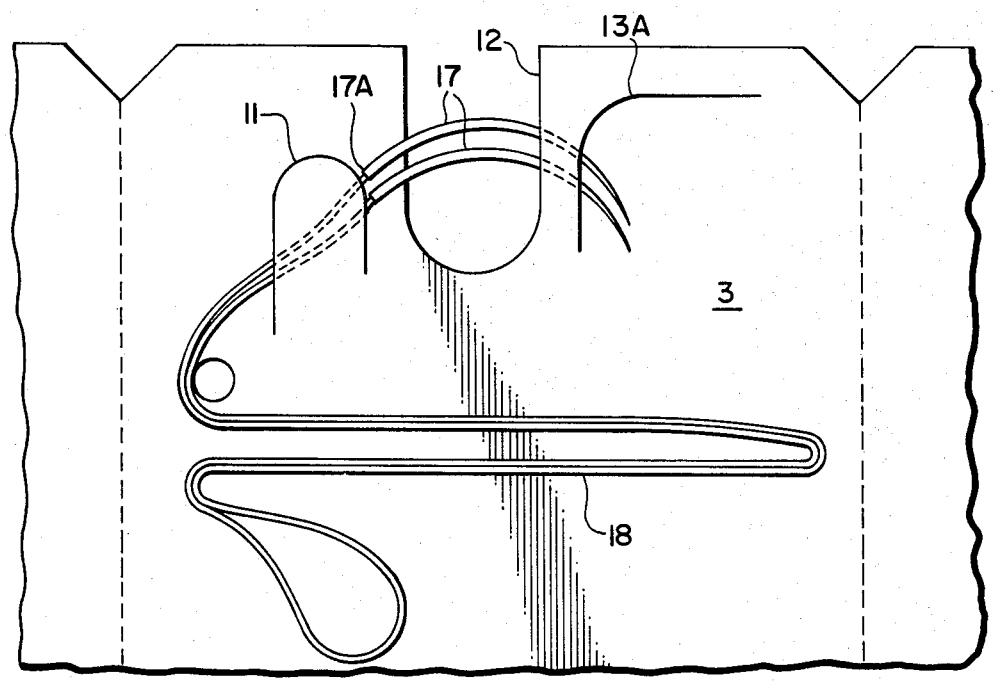
FIG. 4 depicts an embodiment of the invention useful for very small needles, the needle points being held in a curved incised slit rather than an incised aperture, the incised tab holding the suture in place immediately behind the shank of the needles.

FIG. 4 shows an alternative embodiment of the invention designed to be suitable for sutures 18 bearing very small needles 17 on one or both ends. Tab 11 remains the same, but a curved incised slit 13A is used in place of aperture 13 and the shank ends 17A of the small needles 17 fall outside of tab 11 which now holds the suture 18 just behind shank 17A.

To close the suture folder of FIG. 1, with suture 18 and needle 17 in place, the lower portion 2 of panel 1 is folded upwardly along fold line 19 flat against panel 1, panel 1 folded along fold line 16 inwardly onto the face of panel 3 to cover suture 18 and needle 17, then panel 4 is folded inwardly to cover panel 1, the edge 6 of panel 4 is tucked into slit 8, and interlocking edge tabs 5 from panels 3 and 4 are interlocked to complete the closing process.

Figure 5:
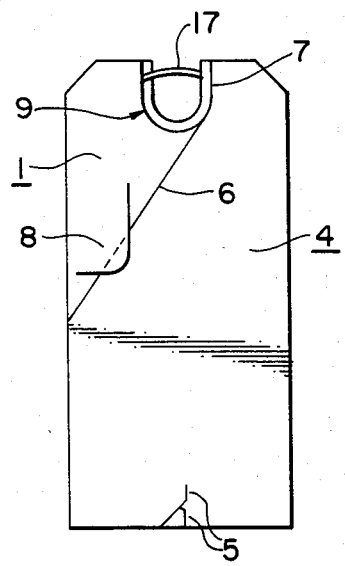
FIG. 5 shows the front side of the folder when folded together, with the edge of the third panel being held by the incised slit of the first panel and the lower edge incised interlocking tabs of the third and second panels interlocked.
Figure 6:
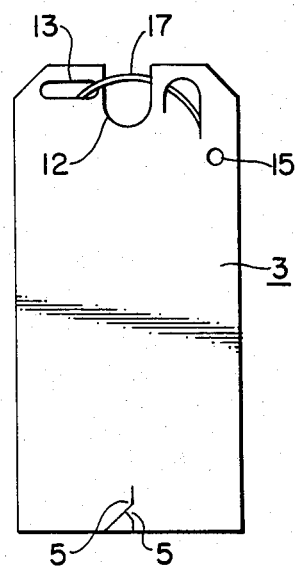
FIG. 6 shows the back side of the folded folder.
Figure 7:
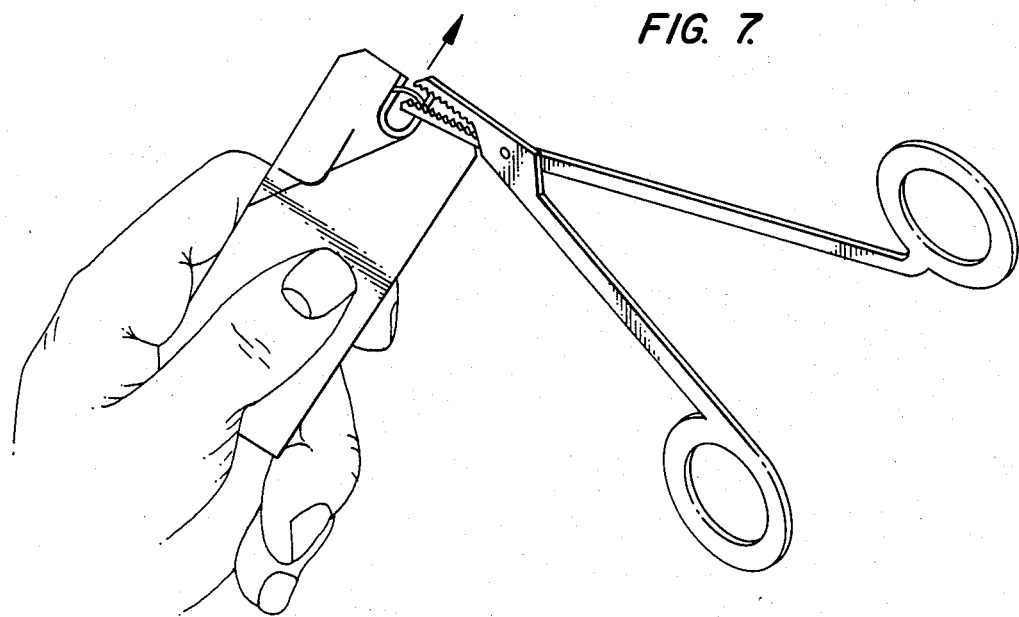
FIG. 7 depicts the easy removal of the needle and suture from either side of the slot. The edge line of the third panel always points to the point of the needles.

FIG. 5 shows the appearance of the front side of the folded suture folder and FIG. 6 shows the back side of the folded suture folder which can be described as self-locking. It can be seen that needles 17 are easily visible and accessible from either side of the folder and can be easily grasped in the slot provided and easily withdrawn along with the attached suture 18. The folder need not be opened for suture removal, as shown in FIG. 7.

Figure 8:
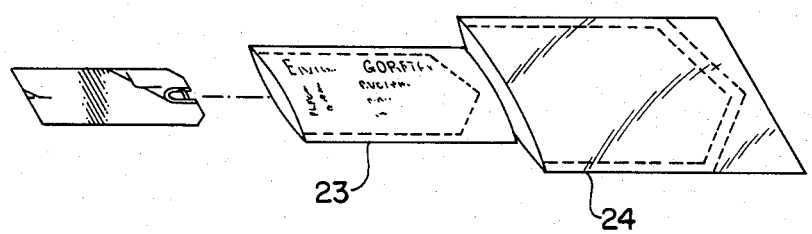
FIG. 8 shows how the paper suture folder is inserted into the inner protective envelope which is sealed and in turn is inserted into the outer clear envelope which is then also sealed.

After closure is complete, the folder is inserted in a preformed inner envelope 23 as seen in FIG. 8, and envelope 23 sealed. Envelope 23 is formed from materials known in the art and usually bears any printed indicia as to source, identity, instructions for use, etc. The chamfered corners 10 of the holder aid in the insertion process. The inner envelope 23 is then sealed in a clear heat-sealable outer envelope 24 to protect the entire contents and may then be cartoned and sterilized, for instance with ethylene oxide gas.

Figure 9:
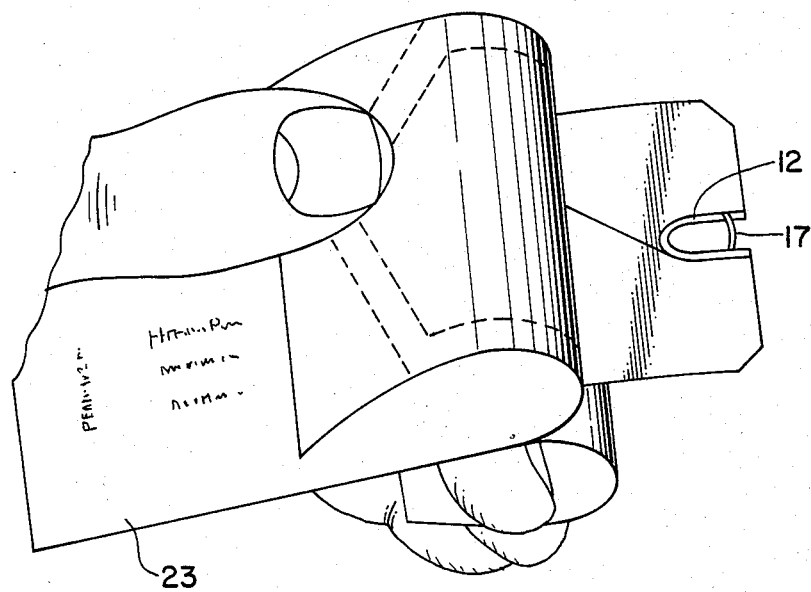
FIG. 9 shows a partially peeled back inner envelope with the folder displaying the needle in the slot for immediate use.

FIG. 9 shows an inner envelope 23 partially peeled back for ready presentation of needle 17 from slot 12 to the user.

The suture folder may be manufactured from medical grades of paper board of an appropriate body or stiffness, such as tag board, solid bleached paper which may be optionally clay coated, or some forms of thin plastic sheeting, such as those made from polyethylene. The inner and outer protective envelopes are usually of heat sealable thermoplastic polymers, such as for instance polyethylene, polyvinyl acetate-ethylene copolymer, or Tyvek (DuPont de Nemours trademark), diolefin polymer, which may also be in the form of composites with paper, aluminum foil, or other appropriate materials. It is preferred that the inner envelope be a composite bearing any required printed indicia and that the outer envelope be of a clear heat-sealable thermoplastic material. The porous expanded polytetrafluoroethylene utilized as suture material is that described in the patents listed above.

Having described the invention in detail and many of the ways it may be practiced, it will be apparent to those skilled in the art that many variations, modifications, and extensions of the basic principles embodied may be made without departing from the spirit or scope of the invention and that the foregoing exemplifications and descriptions are not intended to be limiting of the scope of the invention.

What is claimed is:

1. A folded elongated folder for a surgical suture comprising:

a first panel foldably connected to a second panel along a major edge thereof and a third panel foldably connected along a major edge to said second panel along the opposite major edge of said second panel;

said first panel having optionally chamfered upper corners, a generally U-shaped notch disposed in the center of the upper edge, means for locking said first panel to said third panel when folded, a fold line near the bottom of said first panel to form a foldable flap, and a clearance notch disposed at the lower corner of said first panel adjacent said second panel;

said second panel having optionally chamfered upper corners, a generally U-shaped notch disposed in the center of the upper edge, integral incised means for holding a needle in place disposed on each side adjacent said notch, an optional folder-loading registration aperture disposed below and to the left of said needle holding means adjacent the fold line connecting said first and second panels, and means for locking said second panel with said third panel;

said third panel optionally having a chamfered corner at the fold line between said third panel and the second panel, the major edge opposite said fold line having a contour to avoid overlapping the upper edge generally U-shaped notches of said first and second panels, and means for locking said third panel with said second panel;

said folder when folded with said foldable flap disposed at the bottom of said first panel inwardly folded, said first panel folded to cover said second panel adapted to hold in place a surgical suture disposed thereon and to retain in place any needles attached thereto, said third panel folded to cover said first panel, and said third panel interlocked with said first and second panels at said interlocking means thereon to provide for the dispensing of said suture without opening said folder.

2. A folder of claim 1 wherein the means for interlocking said second and third panels comprise interlocking cut tabs disposed in the lower edge of said panels and the means for locking said first and third panels comprise insertion of the outer contoured major edge of said third panel into an incised slit disposed in the upper half of said first panel, adjacent the fold line with said second panel, said slit configured to receive said edge of said third panel.

3. A folder of claim 1 wherein the means for holding in place needles comprise integral incised tabs, slits and apertures.

4. A folder of claim 1 comprising paper, plastics, and combinations thereof.

5. A folder of claim 1 embodying integral self-locking means.

6. A folder of claim 1 embodying adhesive panel locking means.

7. A folder of claim 1 wherein said panels, said U-shaped notches, and said integral incised means for holding a needle in place vary in size and shape to accommodate a commensurate variance of the size and shape of needles enclosed therein.

8. A folder of claim 1 configured to accommodate sutures having attached none or at least one needle.

9. A folder of claim 1 wherein said suture is placed within said folder by manual means.

10. A folder of claim 1 wherein said suture is placed within said folder by mechanical means.

11. A suture package comprising in combination a folded folder of claim 1 and a suture having attached at least one needle.

12. A suture package of claim 11 wherein the suture is disposed within the folder in a configuration commensurate with the composition and properties of the suture.

13. A suture package of claim 11 wherein the suture is disposed within the folder in a sinusoidal configuration.

14. A suture package of claim 11 wherein the suture comprises porous expanded polytetrafluoroethylene.

15. A suture package of claim 11 wherein the suture is comprised of silk.

16. A suture package of claim 11 wherein the suture is comprised of cotton.

17. A suture package of claim 11 wherein the suture comprises a pliable suitable suture material.

18. A sterilized suture package of claim 11 sealed in at least one protective envelope.

* * * * *